United States Patent [19]

Minami et al.

[11] 4,299,443
[45] Nov. 10, 1981

[54] APPARATUS FOR DETECTING THE DEFECTS OF A PATTERN WITH DIRECTIONAL CHARACTERISTICS USING A FILTER HAVING ARM SECTIONS OF CURVED SHAPE

[75] Inventors: Masana Minami, Kawasaki; Hidekazu Sekizawa, Yokohama, both of Japan

[73] Assignee: Tokyo Shibaura Electric Co., Ltd., Kawasaki, Japan

[21] Appl. No.: 22,842

[22] Filed: Mar. 22, 1979

Related U.S. Application Data

[63] Continuation-in-part of Ser. No. 752,984, Dec. 21, 1976, Pat. No. 4,153,336.

[30] Foreign Application Priority Data

Dec. 22, 1975 [JP] Japan .................................. 50/151951

[51] Int. Cl.³ ...................... G02B 27/38; G01N 21/00
[52] U.S. Cl. ................................ 350/162 SF; 356/71; 356/239
[58] Field of Search .................. 350/162 SF; 356/237, 356/239, 71; 250/550

[56] References Cited

U.S. PATENT DOCUMENTS

| | | | |
|---|---|---|---|
| 3,560,093 | 2/1971 | Montone | 350/166 |
| 3,614,232 | 10/1971 | Mathisen | 350/162 SF |
| 3,658,420 | 4/1972 | Axelrod | 356/71 |
| 3,743,423 | 7/1973 | Heinz et al. | 350/162 SF |
| 3,813,173 | 5/1974 | Teter | 350/162 SF |
| 3,972,616 | 8/1976 | Minami et al. | 356/71 |

Primary Examiner—John K. Corbin
Assistant Examiner—Bruce Y. Arnold
Attorney, Agent, or Firm—Oblon, Fisher, Spivak, McClelland & Maier

[57] ABSTRACT

An apparatus for detecting the defects composed of non-linear components of a subject pattern, includes a laser source for illuminating the subject pattern by a laser beam, a Fourier-transform lens for projecting an information light from the pattern through a spatial filter onto a screen. The filter is placed on the Fourier-transform plane of the Fourier-transformed information light for intercepting the coherent light having information on linear components, the filter having arm sections extending correspondingly to the linear components of said normal pattern, the outer periphery of said arm sections including curved sections of a circular or elliptical shape protruding toward the intersecting point of the arms.

16 Claims, 13 Drawing Figures

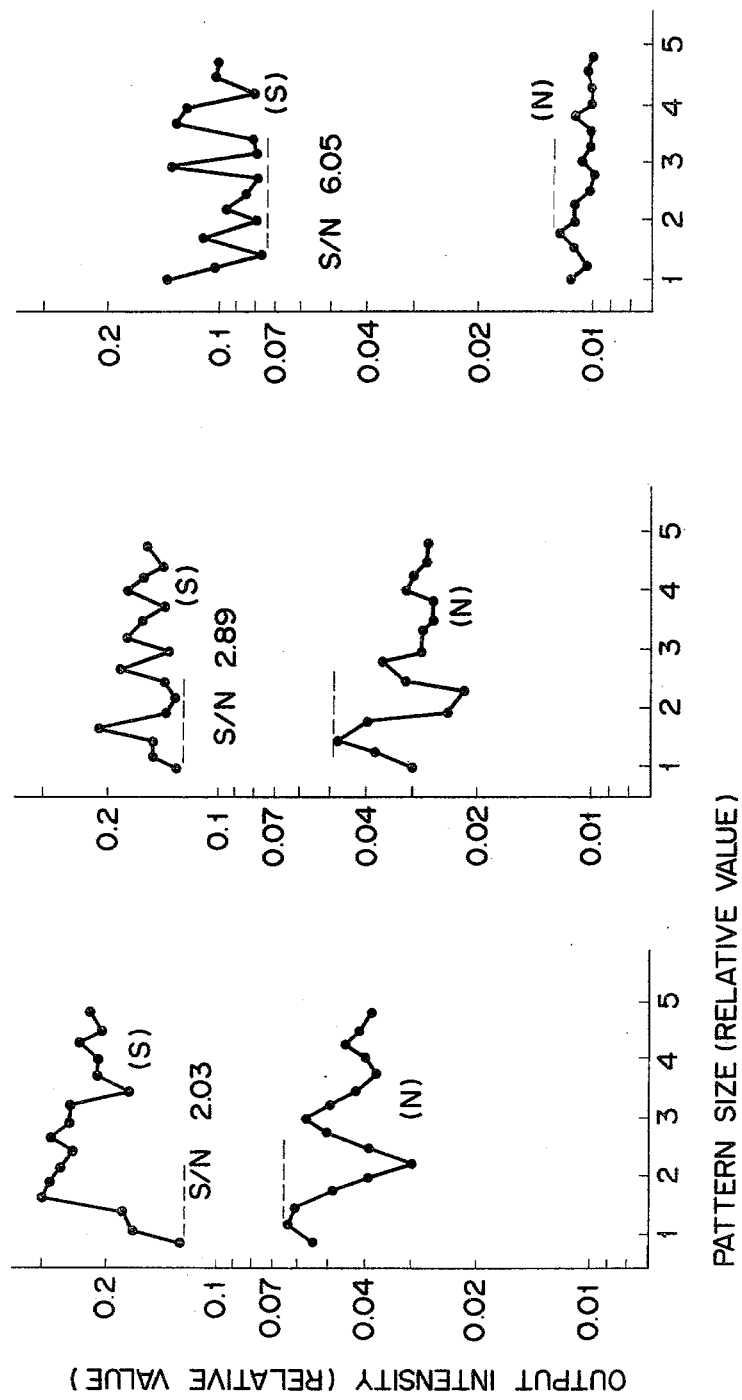

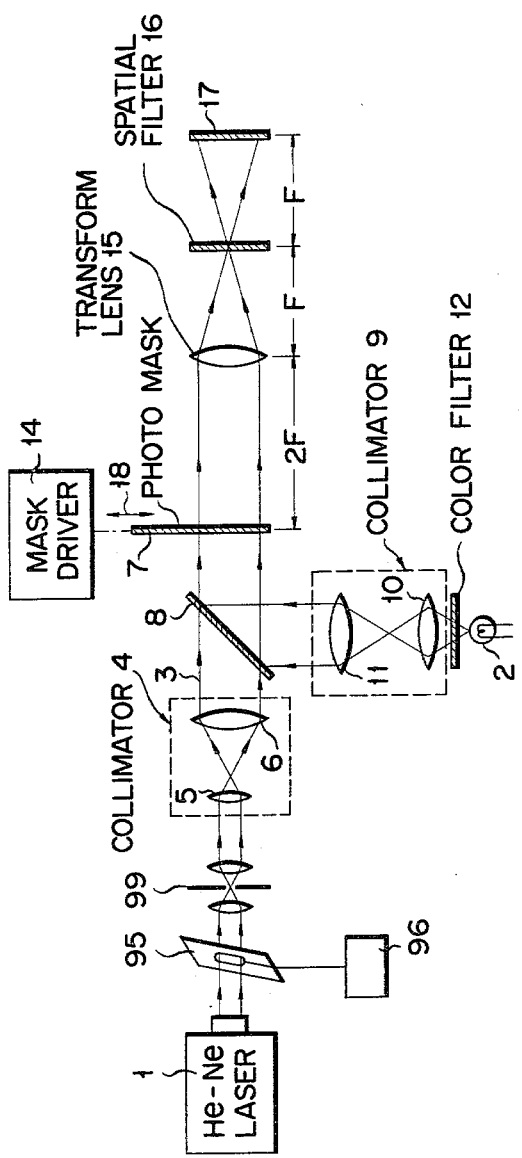

APPARATUS FOR DETECTING THE DEFECTS OF A PATTERN WITH DIRECTIONAL CHARACTERISTICS USING A FILTER HAVING ARM SECTIONS OF CURVED SHAPE

CROSS-REFERENCE TO THE RELATED APPLICATION

This is a continuation-in-part application of United States Patent Application Ser. No. 752,984 filed Dec. 21, 1976, now U.S. Pat. No. 4,153,336.

BACKGROUND OF THE INVENTION

This invention relates to an apparatus for detecting defects of a pattern with directional characters such as IC photo masks, and more specifically to an apparatus for detecting defects employing a spatial filter for filtering optically coherent light.

A detector for detecting defects of patterns with a directional character such as IC photo masks as well as positional information thereof by applying incoherent light and coherent light to the pattern on the same optical axis has already been proposed by the inventors hereof (U.S. Pat. No. 3,972,616 filed on June 27, 1975; patented on Aug. 3, 1976). The device disclosed in the said U.S. Pat. No. 3,972,616 is an available means for detecting the position of a defect on an IC mask. Because of the shape of the spatial filter as a component of the device of the invention, there still remains such problems as the fact that it is difficult to increase the S/N ratio of the brightness (S) of a defect image to the noise (N) or the light intensities of pattern images in the output plane other than the defects to an adequate degree as well as a shortcoming that the noise level may vary substantially with the change of the subject pattern in size.

SUMMARY OF THE INVENTION

An object of this invention is to provide an apparatus for detecting the defects of a pattern with directional characters which may present higher performance or higher S/N ratio as well as low fluctuations in noise level irrespective of any change of the subject pattern in size by solving the aforementioned problems.

BRIEF DESCRIPTION OF THE DRAWINGS

This invention can be more fully understood from the following detailed description when taken in conjunction with the accompanying drawings, in which:

FIGS. 6A, 6B and 6C are graphs showing the measurement results of the relation between the subject pattern sizes and the output intensities for the cases of using the spatial filters as shown in FIGS. 2A, 2B and 3, respectively;

FIGS. 8A and 8B respectively show further embodiments of the device of the present invention employing the spatial filters as shown in FIG. 3.

DESCRIPTION OF THE PREFERRED EMBODIMENTS

There will now be described an apparatus for detecting the defects of a pattern according to an embodiment of this invention with reference to FIGS. 1 and 3.

Figure 1:
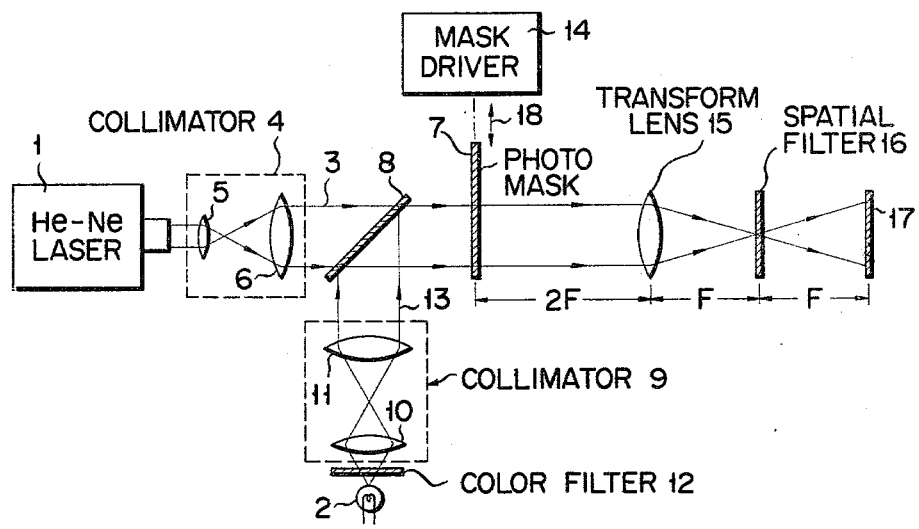
FIG. 1 is a diagram of the apparatus for detecting the defects of the pattern according to the invention.

Referring to FIG. 1, numeral 1 indicates a coherent light source composed of e.g. a He-Ne laser source, from which coherent light is radiated, converted into a parallel light 3 with a predetermined diameter by a collimeter 4 comprising a pair of optical lenses 5 and 6, and then rendered incident upon a half mirror or dichroic mirror 8. The coherent light 3 incident upon the half mirror 8 is transmitted through the mirror 8 and applied to a subject pattern 7 composed of a photo mask for an IC arranged across the optical axis. Also a striped shadow mask for a cathode-ray tube may be used as the subject pattern 7.

Meanwhile, incoherent light radiated from an incoherent light source 2 composed of e.g. an incandescent lamp, after selection of a light with a specific wavelength range by a blue or green color filter 12, is converted into a parallel light 13 with about the same diameter as the aforementioned paralleled coherent light 3, by a collimator 9 comprising a pair of optical lenses 10 and 11 and then rendered incident upon the half mirror 8. The incident light 13 is reflected by the mirror 8 to have an optical axis identical with that of the coherent light 3 as shown in the figure and then rendered incident upon the subject pattern 7.

The photo mask or shadow mask to be used as the subject pattern 7 is composed of a pattern including transparent and opaque sections.

The light transmitted through the subject pattern by the incidence of the coherent light 3 and incoherent light 13 on the information area of the subject pattern is condensed by an optical lens 15 arranged in a filtering optical system. The lens 15, placed at a distance of 2F (F is a Focal length of the lens 15) from the position of the subject pattern, may function as a Fourier transform lens for the coherent information light component of the light transmitted through the subject pattern 7. Accordingly, the coherent information light is Fourier-transformed by the lens 15 and takes a spectral distribution corresponding to the construction of the subject pattern 7 on the Fourier transform surface. That is, as described above, when the subject pattern 7 is composed only of vertical and horizontal straight lines, the said information light has a spectral distribution with directivity in the horizontal and vertical directions. Meanwhile, if the subject pattern 7 has any defects, the spectra of the defects will generally have no specific directivity.

Applying the principle that the Fourier spectrum of a normal pattern is directional, while that of a defect is non-directional, the directional pattern information from the subject pattern 7 is intercepted by a directional filter 16 placed on the condensing side (spectrum side) of the lens 15 and the defect information alone is imaged on a screen 17 through an imaging lens (served by the lens 15 in this embodiment), thereby detected as a defect.

As for the incoherent information light component of the transmitted light from the subject pattern, it has not such a directional distribution as that of the coherent information light in the vicinity of the focal plane of the lens 15, so that it cannot provide a definite filtering effect at the image plane, thereby projecting the whole image of the subject pattern 7 on the screen 17.

Consequently, the existence of defects as well as the positions thereof, may be detected on the screen 17. The defect information may be detected from the pattern formed by the coherent light. The position of the defect may then be determined by examining the image formed by the incoherent light and finding the defect in the image.

When the inspection of defects in the irradiated area of the subject pattern 7 is completed in such a manner as mentioned above, the pattern 7 is shifted by a pattern feeding mechanism (mask driver) 14 and inspected for another area thereof.

Figure 3:
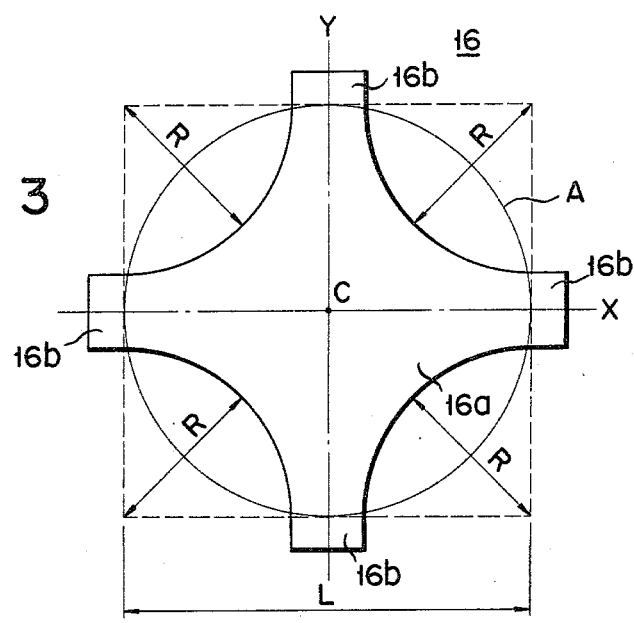
FIG. 3 is a view for illustrating the shapes of spatial filters available for the device of the invention.

The spatial filter 16 for use on the aforementioned device is of such a construction as shown in FIG. 3.

Figure 2A:
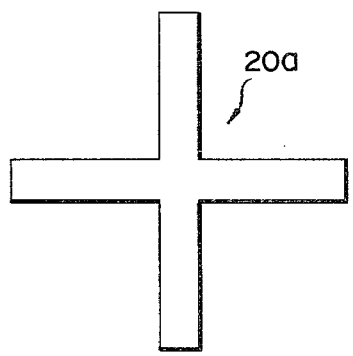
FIGS. 2A and 2B are views for illustrating the shapes of conventional spatial filters.
Figure 2B:
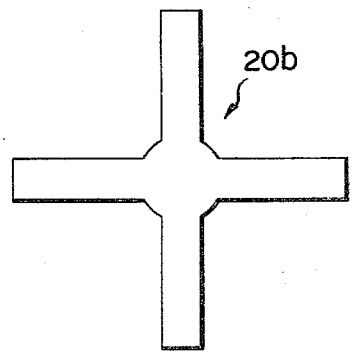

There will now be described the spatial filter with reference to FIGS. 2A and 2B illustrating conventional spacial filters and to FIGS. 6A, 6B and 6C indicating the characteristics of these three filters.

A filter 20a as shown in FIG. 2A is of a cross-shape with a coherent light intercepting area extending horizontally and vertically, and a filter 20b of FIG. 2B has a shape as stated in the aforementioned U.S. Pat. No. 3,972,616. For ease of description, S/N ratio for each case of using the filters of FIGS. 2A and 2B as well as that of FIG. 3 will be explained.

The S/N ratio as mentioned herein is intended to indicate a S/N ratio on the basis of optical signals where S is a brightness of an image of a defect, while N is a brightness appearing on the output surface as a result of the light mainly from the several corners of the subject pattern 7 that is not filtered completely. That is, although the subject pattern may be composed of linear elements alone, its corner sections (as indicated by numerals 51, 52, 53 and 54 in FIG. 5A) are roundish microscopically and such roundness is of the same geometric nature as a defect, so that said filter may not intercept the rays from said corners, allowing them to appear on the output plane as noise. Though, strictly speaking, brightness N may of course include any other brightness such as that of misguided rays, these exist in a substantially negligible amount.

Figure 5A:
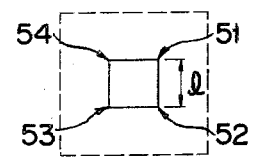
FIGS. 5A and 5B are respectively views for illustrating the shapes of the normal pattern and defect pattern used as standards for measurement of S/N ratio.
Figure 5B:
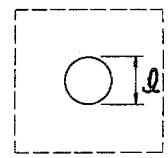

In measuring S/N ratio, a square pattern with a luminous intensity of 1 as shown in FIG. 5A was taken as a standard normal pattern, while a circular pattern with a luminous intensity of 1 as shown in FIG. 5B was taken as a standard defect pattern. A brightness S was to be given at the minimum value of output for each defect pattern size, while a brightness N was to be given at the maximum value of output for each normal pattern size. The results are as shown in FIGS. 6A, 6B and 6C. FIG. 6A illustrates the relation between pattern size and output luminous intensity in the case of using the filter as shown in FIG. 2A, while FIGS. 6B and 6C illustrate the relation between pattern size and output luminous intensity in the cases of using the filters as shown in FIGS. 2B and 3 respectively. That is, as may be seen from these measurement results, the output luminous intensity may fluctuate with the pattern size at a variable fluctuating ratio. As for S/N ratio, S/N=2.03 for FIG. 6A (i.e. where the filter of FIG. 2A is used), S/N=2.89 for FIG. 6B (i.e. where the filter of FIG. 2B is used), and S/N=6.05 for FIG. 6C (i.e. where the filter of FIG. 3 is used.

That is, it is revealed that the S/N ratio with the filter of FIG. 3 is increased by about three times and twice as compared with those with the filters of FIG. 2A and FIG. 2B respectively. Further, the fluctuating ratio of the noise light (leakage light from a normal pattern image through the filter) according to pattern size Nmax/Nmin is about 2.3 for the filter of FIG. 2A and about 2:1 for the filter of FIG. 2B, while that for the filter of FIG. 3 is about 1.2, indicating that the filter of FIG. 3 has a far lower fluctuating ratio of noise luminous intensity as compared with two other filters.

Thus, when either of the filters as shown in FIGS. 2A and 2B is used, the light from the corner section s of IC mask pattern breaks through the filter to appear as noise on the output surface, thereby reducing the S/N ratio at the time of defect detection on the output surface. This noise may vary with the size (construction) of the IC mask pattern. In this way, when the filters as shown in FIGS. 2A and 2B are used, S/N ratio is relatively low and the noise varies substantially with the pattern size, so that the threshold level required for judging defects cannot help but set at an extremely high point in detecting defects. That is, in the case of the filter as shown in FIG. 2A, the fluctuating ratio of noise light is about 2.3 as mentioned above, so that the threshold level is required to be set at a point about 2.3 times higher than the observed noise light level in order to cut out optional noise. If the threshold level is set at such a point, however, the S/N ratio of the filter will be about 2.03 as mentioned above, so it is highly probable that the signal level to indicate a defect will also fall under the threshold level, thereby giving much difficulty in defect detection.

As for the filter as shown in FIG. 2B, the fluctuating ratio of noise light is about 2.1. Accordingly, the threshold level is required to be set at a point about 2.1 times higher than the observed noise light level. In this case, however, the S/N ratio is about 2.89 as mentioned above. Therefore, defect detection may be performed more easily than in the case of using the filter of FIG. 2A, though it may not be deemed to be satisfactory, considering the effects of e.g. flucuations of lasers, drift of the detector, and shading.

Further, in performing visual inspection, ease of defect determination may be reduced for similar reasons.

Meanwhile, when the filter as shown in FIG. 3 is used, the S/N ratio is relatively high as may be seen from FIG. 6C and the fluctuating ratio of noise according to the pattern size is as low as 1.2. Accordingly, with such a filter, the S/N ratio of the filter will be as high as 6.05 if the threshold level is set at a point about 1.2 times higher than the observed noise light level, allowing satisfactory defect detection to be performed.

There will now be described in detail the shape of the filter 16 as shown in FIG. 3 with reference to FIG. 4.

The center C of the filter 16 is on the same optical axis with the center of the effective pupil A of the lens 15.

The filter 16 is constructed of a center portion 16a and four arm sections 16b vertically and horizontally extended from the center portion 16a in a cross like shape. The center portion 16a and arm sections 16b located within the effective pupil A constitute a coherent light intercepting area. The portion lying between the adjacent arm sections 16b is a circular-shaped protruding toward the center of the center portion 16a. The coherent light intercepting area of the filter is defined according to the following four equations $$\begin{cases} \left(X - \frac{L}{2}\right)^2 + \left(Y - \frac{L}{2}\right)^2 \geq R^2 \\ 0 \leq X \leq \frac{L}{2}, 0 \leq Y \leq \frac{L}{2} \end{cases}$$

$$\begin{cases} \left(X + \frac{L}{2}\right)^2 + \left(Y - \frac{L}{2}\right)^2 \geq R^2 \\ -\frac{L}{2} \leq X \leq 0, 0 \leq Y \leq \frac{L}{2} \end{cases}$$

$$\begin{cases} \left(X + \frac{L}{2}\right)^2 + \left(Y + \frac{L}{2}\right)^2 \geq R^2 \\ -\frac{L}{2} \leq X \leq 0, -\frac{L}{2} \leq Y \leq 0 \end{cases}$$

$$\begin{cases} \left(X - \frac{L}{2}\right)^2 + \left(Y + \frac{L}{2}\right)^2 \geq R^2 \\ 0 \leq X \leq \frac{L}{2}, -\frac{L}{2} \leq Y \leq 0 \end{cases}$$

Where X and Y indicate the X-axis and Y-axis of said filter respectively, said X- and Y-axes corresponding to the respective axes of the arm sections of said filter extending in the horizontal and vertical directions, $X=Y=0$ is indicative of the center of said filter, and $9\sqrt{2}/32$ L X $0.85 \leq R \leq 9\sqrt{2}/32$ L X $1.05$, where L is a diameter of an effective pupil of the lens if the effective pupil is circular or $\sqrt{2}/4$ L X $0.85 \leq R \leq \sqrt{2}/4$ L X $1.05$, where L is a length of each side of an effective pupil of the lens if the effective pupil is square.

Figure 4:
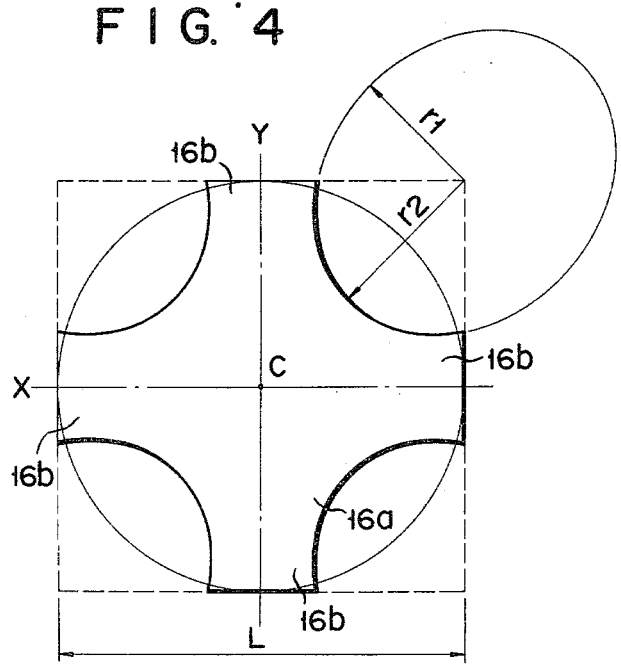
FIG. 4 is a plane view of another spatial filter.

FIG. 4 shows a filter 16 according to another embodiment in which the portion lying between the adjacent arm sections 16b is an elliptical-shape protruding toward the center of the center portion 16a. The coherent light intercepting area of the filter is defined according to the following four equations $$\begin{cases} \frac{(X+Y-L)^2}{r_2^2} + \frac{(-X+Y)^2}{r_1^2} \geq 2 \\ 0 \leq X \leq \frac{L}{2}, 0 \leq Y \leq \frac{L}{2} \end{cases}$$

$$\begin{cases} \frac{(X+Y)^2}{r_1^2} + \frac{(-X+Y-L)^2}{r_2^2} \geq 2 \\ -\frac{L}{2} \leq X \leq 0, 0 \leq Y \leq \frac{L}{2} \end{cases}$$

$$\begin{cases} \frac{(X+Y+L)^2}{r_2^2} + \frac{(X-Y)^2}{r_1^2} \geq 2 \\ -\frac{L}{2} \leq X \leq 0, -\frac{L}{2} \leq Y \leq 0 \end{cases}$$

$$\begin{cases} \frac{(X+Y)^2}{r_1^2} + \frac{(-X+Y+L)^2}{r_2^2} \geq 2 \\ 0 \leq X \leq \frac{L}{2}, -\frac{L}{2} \leq Y \leq 0 \end{cases}$$

Where X and Y indicate the X-axis and Y-axis of said filter respectively, said X- and Y-axes corresponding to the respective axes of the term sections of said filter extending in the horizontal and vertical directions, $X=Y=0$ is indicative of the center of said filter, and $21.2/64$ L X $0.85 \leq r_1 \leq 21.2/64$ L X $1.05$ and $25.5/64$ L X $0.85 \leq r_2 \leq 25.5/64$ L X $1.05$, where L is a diameter of an effective pupil of the lens if the effective pupil is circular or $20.9/64$ L X $0.85 \leq r_1 \leq 20.9/64$ L X $1.05$ and $22.6/64$ L X $0.85 \leq r_2 23$ $22.6/64$ L X $1.05$, where L is a length of each side of an effective pupil of the lens if the effective pupil is square.

In the filter as shown in FIGS. 3 and 4, R and $r_1$, $r_2$ may not necessarily take the above-mentioned values. If the filter value is within a range of 85 to 105% from the above-mentioned values, substantially the same effect is produced. For $R = 9\sqrt{2}/32$ as shown in FIG. 3, for example, R may take a value of $9\sqrt{2}/32$ L (1−0.15) to $9\sqrt{2}/32$ L (1+0.05).

Figure 7:
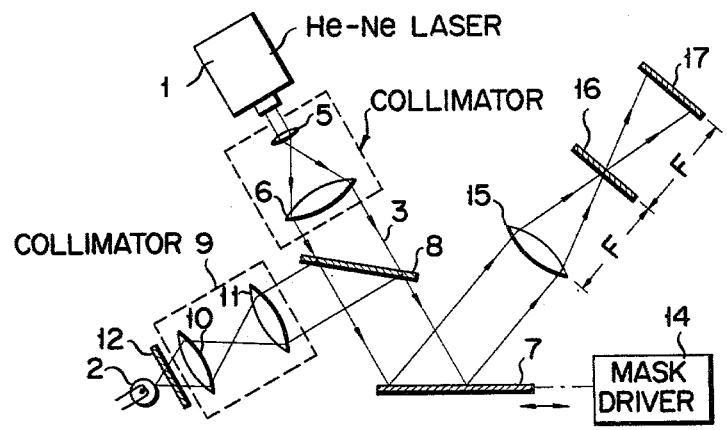
FIG. 7 shows another embodiment of the device of the present invention employing the spatial filters as shown in FIG. 3.

FIG. 7 shows another embodiment of the apparatus of the present invention employing the spatial filters shown in FIGS. 3, 4. In FIG. 7, any parts identical with the corresponding ones as shown in FIG. 1 are indicated by the same numerals.

The apparatus as shown in FIG. 7 may be used suitably when the subject pattern 7 will not transmit light. That is, if the subject pattern is something like a wafer, an element in the IC manufacturing process, the defect for the wafer may be conducted by employing the reflected light from the wafer. The principle and method of flaw detection are similar to the case as described with reference to FIG. 1.

Figure 8A:
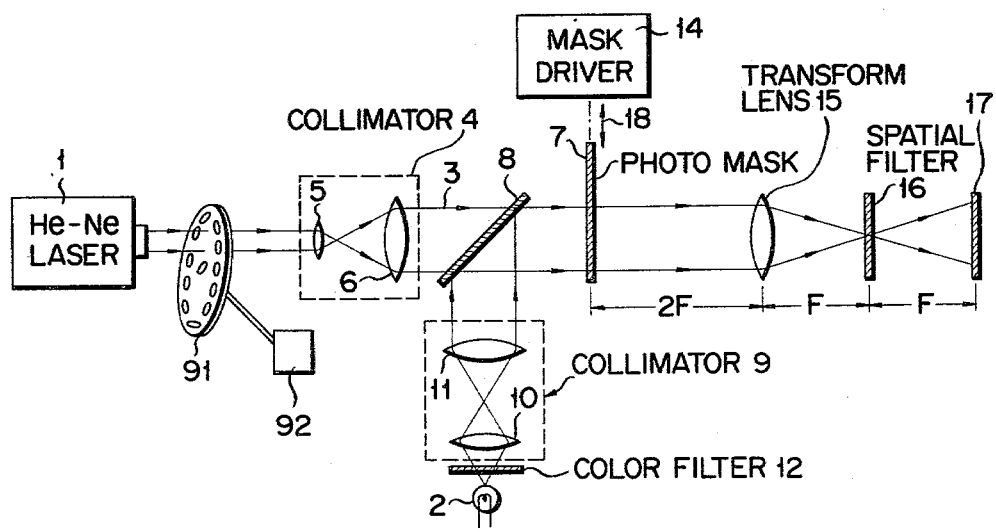

FIGS. 8A and 8B show further embodiments of the apparatus of the present invention. In the same manner as the case of FIG. 7, any parts identical with the corresponding ones as shown in FIG. 1 are indicated by the same numerals as shown in FIG. 1, and the description thereof will be omitted.

Referring now to FIG. 8A, numeral 91 indicates a laser beam chopper with a plurality of holes at the peripheral portions. The beam splitter is arranged between the coherent light source 1 and the collimator 4, and is rotated by a driving source 92 such as a motor at a speed as low as 10 c/s. Consequently, the coherent light is rendered upon the collimator 4 intermittently, providing an on-and-off defect image on the screen 17. This system is especially effective in performing visual defect detection.

Referring now to FIG. 8B, numeral 95 indicates a liquid crystal plate. The liquid crystal plate 95 is controlled by a liquid crystal driving source 96. That is, the amplitude of the coherent light radiated from the coherent light source 1 may be modulated intermittently with the liquid crystal plate 95 by driving the liquid crystal plate 95 intermittently with the liquid crystal driving source 96. Consequently, in the same manner as the case described with reference to FIG. 8A, a defect image is subjected to on-and-off indication on the screen 17. When using the liquid crystal plate, the light radiated from the coherent light source 1 may be scattered by the liquid crystal plate, so that it is advisable to interpose a pair of lenses 97 and 98 and a plate 99 with a pinhole placed substantially on the focus plane of the lens 97 between the liquid crystal plate 95 and the collimator 4 to obtain a better on-off characteristics as shown in FIG. 9B.

Further, the intermittent interception of coherent light as illustrated by FIGS. 8A and 8B also may be performed by means of the coherent light source 1 itself. In this case the coherent light source 1 should be driven intermittently.

Although the filters as shown in FIGS. 3 and 4 may be made of conventional materials such as colored glass and multi-layered dielectric films, they should preferably be formed by using gelatin films for ease of preparations or the like.

Furthermore, in the aforementioned embodiments, coherent and incoherent light are used for detecting both the defect itself and the position thereof and for detecting position alone respectively, though the incoherent light need not be used in detecting the existence of defects alone.

As described above in detail, in the defect detector of this invention, the outer periphery of the intersecting portion between each two adjacent arms of the coherent light intercepting area of the spatial filter is of a curve-shape protruding in the direction toward the center of the filter, so that it may not only intercept securely luminous information of patterns with directional characters but enlarge efficiently the area through which the luminous information indicating defects is transmitted. Consequently, according to the device of this invention, S/N ratio may be increased, while the fluctuating ratio of noise luminous intesity may be reduced.

What we claim is:

1. An apparatus for detecting defects in a pattern having linear straight line features and nonlinear defects comprising:
    (a) a coherent light source for radiating coherent light;
    (b) a collimator for collimating the coherent light radiated from said coherent light source into a light beam with a predetermined diameter and for directing it to said pattern;
    (c) a transform lens for transforming the intensity distribution of transmitted or reflected light from said pattern into a Fourier-transformed pattern; and
    (d) a spatial filter placed in the Fourier-transform plane of said transform lens which prevents transmission of the coherent light containing information of said linear straight line features of said pattern, said filter having a light intercepting area including a plurality of arm sections extending in the horizontal and vertical directions from a common point of intersection corresponding to the linear straight line features of said subject pattern and a portion lying between the two adjacent arm sections being of a circular shape protruding toward the center of said filter wherein the coherent light intercepting area of said spatial filter is defined according to the following four equations $$\begin{cases} \left(X-\frac{L}{2}\right)^2 + \left(Y-\frac{L}{2}\right)^2 \geq R^2 \\ 0 \leq X \leq \frac{L}{2}, 0 \leq Y \leq \frac{L}{2} \end{cases}$$

$$\begin{cases} \left(X+\frac{L}{2}\right)^2 + \left(Y-\frac{L}{2}\right)^2 \geq R^2 \\ -\frac{L}{2} \leq X \leq 0, 0 \leq Y \leq \frac{L}{2} \end{cases}$$

$$\begin{cases} \left(X+\frac{L}{2}\right)^2 + \left(Y+\frac{L}{2}\right)^2 \geq R^2 \\ -\frac{L}{2} \leq X \leq 0, -\frac{L}{2} \leq Y \leq 0 \end{cases}$$

$$\begin{cases} \left(X-\frac{L}{2}\right)^2 + \left(Y+\frac{L}{2}\right)^2 \geq R^2 \\ 0 \leq X \leq \frac{L}{2}, -\frac{L}{2} \leq Y \leq 0 \end{cases}$$

where X and Y indicate the X-axis and Y-axis of said filter respectively, said X- and Y-axes corresponding to the respective axes of the arm sections of said filter extending in the horizontal and vertical directions, $X=Y=0$ is indicative of the center of said filter and, in the situation where the effective pupil is circular, $9\sqrt{2}/32\ L\times0.85 \leq R \leq 9\sqrt{2}/32\ L\times1.05$ where L is a diameter of an effective pupil of the lens or in the situation where the effective pupil is square $\sqrt{2}/4\ L\times0.85 \leq R \leq \sqrt{2}/4\ L\times1.05$ where L is a length of each side of an effective pupil of the lens.

2. An apparatus according to claim 1 which further comprises an incoherent light source radiating an incoherent light and means for directing the incoherent light from the light source to said pattern in compliance with the optical axis of said coherent light.

3. An apparatus according to claim 2 wherein said coherent light source is a Helium-Neon laser and said incoherent light source is an uncandescent lamp.

4. An apparatus according to claim 3 which further comprises a color filter located across the optical path of the incoherent light radiated from said incoherent light source.

5. An apparatus according to claim 4 wherein said color filter is a blue or green, gelatin filter.

6. An apparatus according to claim 1 which further comprises control means for chopping, intermittently, the coherent light radiated from said coherent light source.

7. An apparatus according to claim 6 wherein said control means includes a beam chopper with a plurality of holes therein, placed adjacent to said coherent light source, and driving means for rotating said beam chopper.

8. An apparatus according to claim 7 wherein said control means includes a liquid crystal plate placed adjacent to said coherent light source, a lens system for collimating the coherent light transmitted through said liquid crystal plate, and a plate with a pinhole arranged in said lens system.

9. An apparatus for detecting defects in a pattern having linear straight line features and nonlinear defects comprising:
    (a) a coherent light source for radiating coherent light;
    (b) a collimator for collimating the coherent light radiated from said coherent light source into a light beam with a predetermined diameter and for directing it to said pattern;
    (d) a transform lens for transforming the intensity distribution of transmitted or reflected light from said pattern into a Fourier-transformed pattern; and
    (d) a spatial filter placed in the Fourier-transform plane of said transform lens which prevents transmission of the coherent light containing information of said linear straight line features of said pattern, said filter having a light intercepting area including a plurality of arm sections extending in the horizontal and vertical directions from a common point of intersection corresponding to the linear straight line features of said subject pattern and a portion lying between the two adjacent arm sections being of an elliptical-shape protruding toward the center of said filter wherein the coherent light intercepting area of said spatial filter is defined according to the following four equations $$\begin{cases} \dfrac{(X+Y-L)^2}{[r_1^2]\,r_2^2} + \dfrac{(-X+Y)^2}{[r_2^2]\,r_1^2} \geq 2 \\ 0 \leq X \leq \dfrac{L}{2},\ 0 \leq Y \leq \dfrac{L}{2} \end{cases}$$

$$\begin{cases} \dfrac{(X+Y)^2}{[r_2^2]\,r_1^2} + \dfrac{(-X+Y-L)^2}{[r_1^2]\,r_2^2} \geq 2 \\ -\dfrac{L}{2} \leq X \leq 0,\ 0 \leq Y \leq \dfrac{L}{2} \end{cases}$$

$$\begin{cases} \dfrac{(X+Y-L)^2}{[r_1^2]\,r_2^2} + \dfrac{(X-Y)^2}{[r_2^2]\,r_1^2} \geq 2 \\ -\dfrac{L}{2} \leq X \leq 0,\ -\dfrac{L}{2} \leq Y \leq 0 \end{cases}$$

$$\begin{cases} \dfrac{(X+Y)^2}{[r_2^2]\,r_1^2} + \dfrac{(-X+Y+L)^2}{[r_1^2]\,r_2^2} \geq 2 \\ 0 \leq X \leq \dfrac{L}{2},\ -\dfrac{L}{2} \leq Y \leq 0 \end{cases}$$

where X and Y indicate the X-axis and Y-axis of said filter respectively, said X- and Y-axes corresponding to the respective axes of the arm sections of said filter extending in the horizontal and vertical directions and, in the situation where the effective pupil is circular 21.2/64 L×0.85≦$r_1$≦21.2/64 L×1.05 and 25.5/64 L×0.85=$r_2$≦25.5/64 L×1.05
where L is a diameter of an effective pupil of the lens or in the situation where the effective pupil is square 20.9/64 L×0.85≦$r_1$20.9/64 L×1.05 and 22.6/64 L×0.85≦$r_2$≦22.6/64 L×1.05 where L is a length of each side of an effective pupil of the lens.

10. An apparatus according to claim 9 which further comprises an incoherent light source radiating an incoherent light and means for directing the incoherent light from the light source to said pattern in compliance with the optical axis of said coherent light.

11. An apparatus according to claim 10 wherein said coherent light source is a Helium-Neon laser and said coherent light source is an incandescent lamp.

12. An apparatus according to claim 11 which further comprises a color filter located across the optical path of the incoherent light radiated from said incoherent light source.

13. An apparatus according to claim 12 wherein said color filter is a blue or green, gelatin filter.

14. An apparatus according to claim 9 which further comprises control means for chopping, intermittently, the coherent light radiated from said coherent light source.

15. An apparatus according to claim 14 wherein said control means includes a laser beam chopper with a plurality of holes therein, placed adjacent to said coherent light source, and driving means for rotating said beam chopper.

16. An apparatus according to claim 15 wherein said control means includes a liquid crystal plate placed adjacent to said coherent light source, a lens system for collimating the coherent light transmitted through said liquid crystal plate, and a plate with a pinhole arranged in said lens system.

* * * * *